(12) United States Patent
Gladney et al.

(10) Patent No.: US 6,792,819 B2
(45) Date of Patent: *Sep. 21, 2004

(54) METHOD AND SYSTEM FOR ANALYZING MOTION TRANSFERRED TO A SUBJECT ON A SLEEPING SURFACE

(75) Inventors: Rick F. Gladney, Fairburn, GA (US); James Martin Arrowood, Gainesville, GA (US)

(73) Assignee: Dreamwell, Ltd., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/437,277

(22) Filed: May 12, 2003

(65) Prior Publication Data

US 2004/0003669 A1 Jan. 8, 2004

Related U.S. Application Data

(63) Continuation of application No. 09/898,747, filed on Jul. 3, 2001, now Pat. No. 6,561,047.

(51) Int. Cl.[7] .............................. G01N 3/34; G01N 3/42
(52) U.S. Cl. .......................... 73/865.3; 73/488; 73/490; 73/503; 73/504.03; 73/51; 73/511; 73/514.01; 73/514.26
(58) Field of Search .......................... 73/488, 490, 503, 73/504.03, 510, 511, 514.01, 514.26, 865.3

(56) References Cited

U.S. PATENT DOCUMENTS

| | | | | |
|---|---|---|---|---|
| 2,154,561 A | * | 4/1939 | Breer et al. .................. 73/819 |
| 2,327,829 A | * | 8/1943 | Sternberg et al. ............. 73/161 |
| 2,378,039 A | * | 6/1945 | Schenker ..................... 73/172 |
| 2,644,332 A | * | 7/1953 | Ulrich ........................ 73/172 |
| 4,004,457 A | * | 1/1977 | Eide et al. ................... 73/818 |
| 4,140,008 A | * | 2/1979 | Golembeck et al. ........... 73/78 |
| 4,669,302 A | * | 6/1987 | Wagner et al. ............... 73/172 |
| 5,010,772 A | * | 4/1991 | Bourland et al. ...... 73/862.046 |
| 5,148,706 A | * | 9/1992 | Masuda et al. .............. 73/172 |
| 5,253,656 A | * | 10/1993 | Rincoe et al. .............. 600/595 |
| 5,396,510 A | * | 3/1995 | Wilson ........................ 356/28 |
| 6,062,216 A | * | 5/2000 | Corn ..................... 128/204.23 |
| 6,295,675 B1 | * | 10/2001 | Ellis et al. ..................... 5/710 |
| 6,315,740 B1 | * | 11/2001 | Singh ........................ 600/595 |

FOREIGN PATENT DOCUMENTS

| | | | | |
|---|---|---|---|---|
| DE | 4139697 A1 | * | 6/1993 | ............ A47C/25/00 |
| WO | WO 200051470 A1 | * | 9/2000 | ............ A47C/31/12 |

OTHER PUBLICATIONS

ASTM Designation: F 1566–94, "Standard Test Methods for Evaluation of Innersprings and Boxsprings" (Published Jan. 1995).*

* cited by examiner

Primary Examiner—Hezron Williams
Assistant Examiner—David A. Rogers
(74) Attorney, Agent, or Firm—Ropes & Gray LLP

(57) ABSTRACT

A method and system for analyzing the transfer of motion to a subject on a sleeping surface. A mattress is positioned on a frame, and a subject is positioned on the mattress. A sensor is placed in communication with the subject. The surface adjacent the subject is moved by means of a moving mass, and the sensor detects the motion of the subject. Motion transferred to the subject as a result of the mattress moving is measured and recorded.

16 Claims, 2 Drawing Sheets

METHOD AND SYSTEM FOR ANALYZING MOTION TRANSFERRED TO A SUBJECT ON A SLEEPING SURFACE

CROSS-REFERENCE TO RELATED APPLICATIONS

This application is a continuation of U.S. application Ser. No. 09/898,747, filing date Jul. 3, 2001, now U.S. Pat. No. 6,561,047, naming James M. Arrowood and Richard F. Gladney as inventors, the specification of which is herein incorporated by reference.

BACKGROUND OF THE INVENTION

This invention relates to a method and apparatus for analyzing the amount of motion transferred to a subject resting on one area of a mattress as a result of movement imparted to the mattress in another adjacent area by a moving mass. When two people sleep in a single bed, comprising a mattress and a foundation, the bed cannot always comfortably accommodate them, particularly if one of the people is of relatively large stature or if one of the people is a relatively light sleeper or a restless sleeper. Because of the close proximity, movement by one occupant of the bed is transferred by the bed to and tends to wake up or disturb the other occupant. The less motion transferred from one occupant to the other occupant, the better the mattress or combination of mattress and foundation is for the occupants.

In designing beds, including mattresses and foundations, predicting which design will transfer the least amount of motion from one occupant to the other is often difficult. Thus, there is a need for a method and system for measuring the movement transferred from one bed occupant to another and thereby create a basis for evaluating one mattress or combination of mattress and foundation design versus another mattress or combination of mattress and foundation design with respect to motion transfer.

SUMMARY OF THE INVENTION

The present invention is a method and system for analyzing the amount of motion transferred to a subject resting on one area of a mattress as a result of a moving mass on an adjacent area of the mattress. The method includes the steps of supporting a mattress on a frame, positioning the subject on one area of the mattress, locating sensors in proximity to the subject to detect the movement of the subject, moving a mass on an adjacent surface area of the mattress, and measuring and recording the motion transferred to the subject as a result of the mass moving adjacent the subject. Once the amount of motion transferred to the subject has been measured and recorded, a transferred motion value, or other benchmark value, can be calculated so that the amount of motion transferred by one mattress or combination of mattress and foundation can be compared to the amount of motion transferred by another mattress or combination of mattress and foundation. In accordance with the present invention, the designs of the mattresses and foundations, and combinations thereof, can be compared to determine which designs transfer the least amount of motion.

For a better understanding of the present invention, together with other and further objects thereof, reference is made to the following description, taken in conjunction with the accompanying drawings, and the appended claims.

DETAILED DESCRIPTION OF THE INVENTION

The present invention is directed to a method and system for analyzing the amount of motion transferred to a subject resting on a mattress resulting from the movement of a mass on the mattress adjacent to, but displaced from, the subject. The movement transferred from one bed occupant to another is quantified by measuring the motion transferred to a mannequin as the result of moving a mass, such as a roller, which produces movement in another area of the mattress adjacent the mannequin. The mannequin represents a human of average body size and weight resting on one area of the mattress surface. In one test procedure, the moving mass is provided by a standard rollator (ASTM F1566) that contacts one lateral side of the mattress. As the roller of the rollator moves toward and away from the mannequin, the amplitude, acceleration, and velocity of the horizontal and vertical displacement of the mannequin positioned on the other lateral side of the mattress are measured. Several tests are run over time, and the displacement data is processed to produce transferred motion values which represent quantitatively the performance of the mattress or combination of mattress and foundation with respect to motion transfer.

The amplitude, acceleration, and velocity of the displacement of the mannequin will vary, depending on the type of mattress and foundation used. A woven wire inner spring mattress will transfer motion differently than a marshal coil-type mattress, although both types of mattress constructions can be tested in accordance with the invention. The types of foundations, such as box springs, used (e.g., continuous wire or module) also will affect the motion transferred, but again, both types can be tested in accordance with the invention. From transferred motion values, mattresses or combinations of mattresses and foundations of various constructions can be compared one to another in order to determine which construction transfers the least amount of motion.

Figure 1:
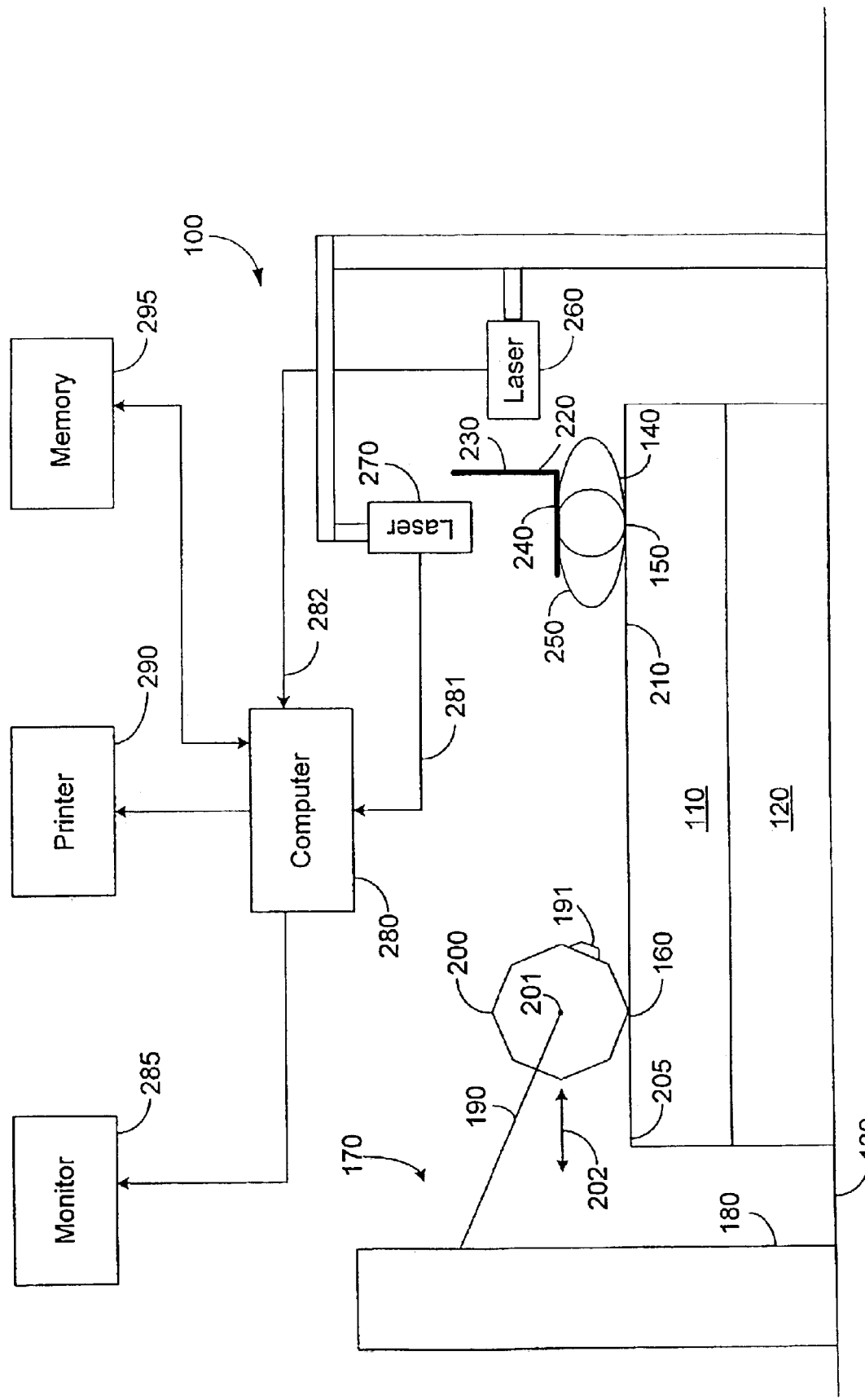
FIG. 1 is a schematic view of an illustrative embodiment of the present invention.

FIG. 1 depicts a system 100 for measuring the amount of movement transferred to a subject 140 by the combination of a mattress 110 and foundation 120. The foundation 120 is supported on the floor 130. The mattress 110 is in turn supported on the foundation 120. The subject 140 rests at a position 150 on the mattress 110. In FIG. 1, the subject 140 is shown oriented from head to toe along the Z-axis of FIG. 1. The subject 140 can be a mannequin, or any other suitable object that represents the average human body in size and weight. A device 170 imparts motion to an area 160 of the mattress 110. The area 160 extends from a point 205 that is adjacent to one edge of the mattress 110 to a point 210 that is adjacent to, but displaced from, the subject 140 by several inches. The device 170 includes an eight sided roller 200, or any other suitable moving mass for transmitting movement to the area 160 of the mattress 110.

In connection with the present invention, the device 170 is a standard rollator. The operation of the rollator is described in ASTM F1566, and that standard is incorporated herein by reference. The rollator includes a frame 180 and an actuator arm 190 attached to the roller 200. The roller 200 has an axis 201 which extends parallel to the Z-axis of FIG. 1. The ASTM F1566 standard calls for a six sided roller which weighs about 240 pounds. The present invention utilizes an eight sided roller, but a six sided roller is considered useful in connection with the present invention.

As can be seen in FIG. 1, the roller 200 also has a bump 191 affixed to one surface. The bump 191 is about once to inches high and about six inches square at its base. The bump 191 is used to simulate the hips of and occupant as the occupant roles from side to side.

In operation, the actuator arm 190 moves the roller 200 horizontally, back and forth (arrow 202), between a first point 205 and a second point 210 within the area 160 of the mattress 110. The point 210 should be within about three inches of the subject 140. The actuator arm 190 is set at an angle of about 0 to 5 degrees to the horizontal surface of the mattress 110. The roller 200 moves back and forth along the surface of the mattress 110 from point 205 to point 210 at a speed of 20 cycles per minute. The closer the roller 200 is to the subject 140, the greater the transmission of motion to the subject 140. While the system 100 in FIG. 1 shows the roller moving toward and away from the subject 140, the method of the present invention also contemplates transmitting motion to the mattress in the area 160 by other means. For example, the roller could be set up to roll parallel to the length of the subject 140 (along the Z-axis). In addition, movement of the mattress 110 in area 160 could be accomplished by dropping a weight onto the mattress 110 in that area. Any moving mass that imparts a consistent pattern of movement to the area 160 of the mattress 110 is useful in connection with the present invention.

In order to detect the motion transferred from the roller 200 to the subject 140, a target 220, having a vertical face 230 and horizontal face 240 is attached to the chest 250 of the subject 140. Lasers 260 and 270 are positioned above the subject 140. The laser 260 is focused on the vertical face 230 of the target 220, and the laser 270 is focused on the horizontal face 240 of the target 220. The laser 260 captures the horizontal displacement of the subject 140, and the laser 270 captures the vertical displacement of the subject 140. The lasers 260 and 270 produce signals that are proportional to the horizontal and vertical displacement of the subject 140.

The signals representing the vertical displacement and horizontal displacement of the subject 140 are connected to a computer 280 via lines 281 and 282. In accordance with the present invention, the computer 280 is a general-purpose digital computer and calculates transferred motion values for the combination of the mattress 110 and the foundation 120. The calculated transferred motion values can then be displayed on a monitor 285, printed on a printer 290, or stored in a memory 295 for later recall. Particularly, the transferred motion values from a number of mattress constructions or combinations of mattress and foundation constructions can be used to determine which mattress construction or combinations of mattress and foundation constructions are optimum in terms of the least amount of transferred motion.

In one embodiment, the computer 280 is a general-purpose digital computer which uses a standard tester application program sold under the trademark "LABVIEW", marketed by National Instruments Corporation in Austin, Tex. Briefly described, the LABVIEW application program allows a user to create programs in block diagram form by use of a graphical programming language. LABVIEW includes libraries containing functions and development tools, which are designed for data acquisition and instrument control. The LABVIEW programs are referred to as virtual instruments (VIs) because they can appear and operate like actual instruments. A VI includes an interactive user interface, a dataflow diagram that serves as the source code, and icon connections that allow a VI to be called from higher level VIs. LABVIEW is based on the concept of modular programming, so it allows the user to divide an application into a series of tasks, which the user can then divide again into subtasks. The user builds a VI to accomplish each subtask, and then combines each VI on another block diagram to accomplish a larger task. Particularly, the LABVIEW program can be used to implement the method of the present invention as set forth in the flowchart in FIG. 2.

Figure 2:
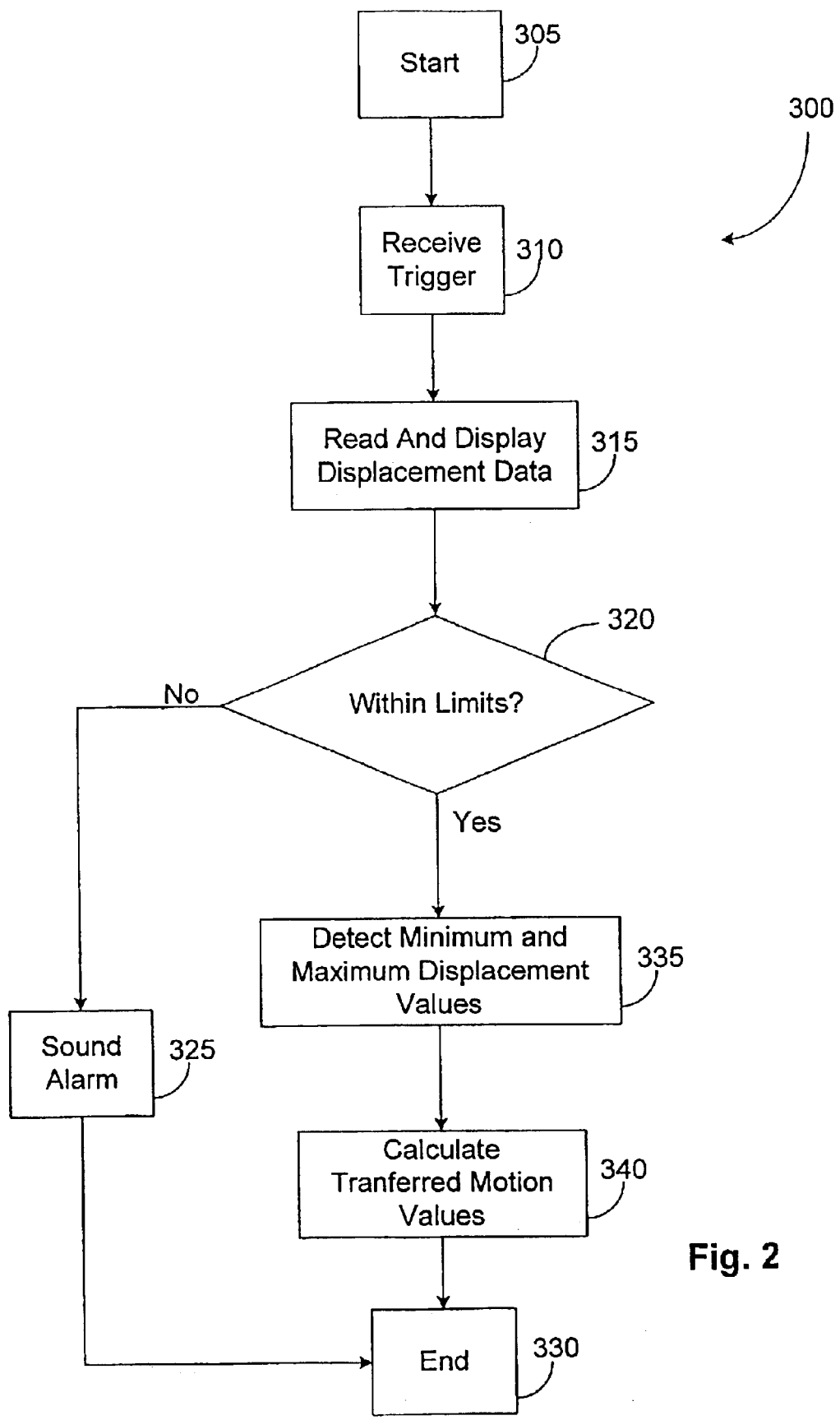
FIG. 2 is a flow chart illustrating a method for analyzing motion transferred to a subject on a mattress.

FIG. 2 is a flow chart illustrating a method 300 for analyzing the transfer of motion to a subject 140 on the mattress 110 and foundation 120. Those skilled in the art will appreciate that the method 300 in FIG. 2 may be implemented by the computer 280 utilizing the programming capabilities of the LABVIEW application program module. Other application program modules may be used as well to implement the method shown in FIG. 2

As shown in FIG. 2, the method 300 begins at step 305 and proceeds to step 310 where a trigger is received by the application program module, such as LABVIEW as previously described. The trigger is an indication to the application program module to begin the method 300. The trigger may be generated, for example, when the user positions the mouse cursor and clicks on a start icon on the screen. After the trigger is received by the application program module at step 310, the vertical displacement values from the laser 270 and the horizontal displacement values from the laser 260 are read and displayed at step 315. Next, at decision step 320, a determination is made as to whether the vertical and horizontal displacements or within ranges between upper limits and lower limits. Each of these limit values are user-selectable values. The upper and lower limits for the for the vertical and horizontal displacements are set by reference to approximately 50 peaks and approximately 50 valleys on the displayed displacement values. Once the preselected ranges for the horizontal and vertical displacements is set, the computer begins acquiring vertical and horizontal displacement data for a period of from 3 to 10 minutes.

If, at decision step 320, the vertical and horizontal displacement values fall outside the preselected ranges during the data acquisition, then an alarm sounds at step 325, and the method ends at step 330. If, on the other hand, the horizontal displacement values remain within the preselected ranges during the data acquisition, then the minimum and maximum displacement values (horizontal and vertical) are detected in step 335. At step 340, during a user-selectable time period, the computer 280 calculates transferred motion values which may include among other benchmark values: a statistical mean (average), the standard deviation, a count, or a histogram. The calculated transferred motion values represent a benchmark for the particular mattress or mattress and foundation that define the amount of motion transferred by the mattress or mattress and foundation. That data may be viewed on monitor 285 or printed on printer 290. The data is also stored in memory 295 so that it may be recalled for future comparison with similar data generated for a different combination of mattress and foundation construction. From such comparisons, one can determine which mattress or mattress and foundation combination provides the least amount of motion transfer.

While there has been described what is believed to be the preferred embodiment of the present invention, those skilled in the art will recognize that other further changes and modifications may be made thereto without departing from the spirit of the invention, and it is intended to claim all such changes and modifications as fall within the true scope of the invention.

We claim:

1. A method of selecting a mattress/foundation combination with a minimum motion transfer between subjects positioned on a common mattress surface, comprising the steps of:

supporting a mattress on a foundation;

positioning an object representative of a first subject on the common mattress surface at a first location;

moving the common mattress surface adjacent to the object;

measuring a displacement of a place on the object relative to a reference location in response to moving the common mattress surface; and recording the measured displacement for a plurality of mattress/foundation combinations to determine at least one mattress/foundation combination that has the minimum motion transfer.

2. The method of claim 1, wherein measuring includes measuring the displacement in at least one of a horizontal and vertical direction.

3. The method of claim 1, further including determining from the measured displacement at least one of a velocity and acceleration of the place on the object.

4. The method of claim 1, wherein moving the common surface includes applying a rollator.

5. The method of claim 1, wherein the object is a mannequin and the place comprises a target located on the mannequin.

6. The method of claim 4, wherein the rollator is moved on the common surface in a direction toward and away from the object.

7. The method of claim 4, wherein the rollator simulates a size and weight of a person.

8. A method for quantifying a performance of a mattress, comprising:

exciting a first motion on a mattress surface at a first location;

providing a stationary surface that is unaffected by any movement;

providing at least one displaceable surface on or above the mattress upper surface at a second location spaced apart from the first location;

detecting a displacement of the at least one displaceable surface relative to the stationary surface that represents a movement transferred from motion at the first location;

comparing the detected displacement with a reference value to quantify the performance.

9. The method of claim 8, and further comprising associating performance values based on the comparing.

10. The method of claim 9, wherein a highest performance value is associated with a mattress having a smallest transferred movement.

11. The method of claim 8, wherein detecting the displacement includes directing a beam of optical radiation on the at least one displaceable surface and measuring a reflected beam reflected from the at least one displaceable surface to determine the displacement of the at least one displaceable surface relative to the stationary surface.

12. The method of claim 11, wherein the beam of optical radiation is a laser beam.

13. The method of claim 8, wherein the at least one displaceable surface includes a horizontal surface parallel to the mattress surface and a vertical surface perpendicular to the mattress surface.

14. The method of claim 8, wherein detecting the displacement includes computing from the displacement at least one of a velocity and an acceleration of the at least one displaceable surface relative to the stationary surface.

15. The method of claim 8, wherein the first motion is excited in at least one of a direction parallel and perpendicular to the mattress surface.

16. The method of claim 8, wherein the first motion is excited parallel to the mattress surface and in a direction towards the second location.

* * * * *